(12) United States Patent
Lee et al.

(10) Patent No.: US 10,870,783 B2
(45) Date of Patent: *Dec. 22, 2020

(54) SURFACTANT ADHESIVE COMPOSITION

(71) Applicant: KOLLODIS BIOSCIENCES, INC., North Augusta, SC (US)

(72) Inventors: Sang Jae Lee, Seoul (KR); Bong Jin Hong, Pohang-si (KR)

(73) Assignee: KOLLODIS BIOSCIENCES, INC., North Augusta, SC (US)

( * ) Notice: Subject to any disclaimer, the term of this patent is extended or adjusted under 35 U.S.C. 154(b) by 9 days.

This patent is subject to a terminal disclaimer.

(21) Appl. No.: 15/750,967

(22) PCT Filed: Aug. 8, 2016

(86) PCT No.: PCT/KR2016/008677
§ 371 (c)(1),
(2) Date: Feb. 7, 2018

(87) PCT Pub. No.: WO2017/026759
PCT Pub. Date: Feb. 16, 2017

(65) Prior Publication Data
US 2018/0327643 A1 Nov. 15, 2018

(30) Foreign Application Priority Data
Aug. 7, 2015 (KR) .................. 10-2015-0111504

(51) Int. Cl.
*C09J 189/00* (2006.01)
*C07K 7/08* (2006.01)
*C07K 14/435* (2006.01)
*C07K 7/06* (2006.01)

(52) U.S. Cl.
CPC .............. *C09J 189/00* (2013.01); *C07K 7/06* (2013.01); *C07K 7/08* (2013.01); *C07K 14/43504* (2013.01); *C07K 2319/00* (2013.01)

(58) Field of Classification Search
CPC ................... C07K 14/43504; C07K 2319/00; C07K 7/06; C07K 7/08; C09J 189/00
See application file for complete search history.

(56) References Cited

U.S. PATENT DOCUMENTS

| | | | |
|---|---|---|---|
| 5,230,823 A | 7/1993 | Wise et al. | |
| 5,368,756 A | 11/1994 | Vogel et al. | |
| 5,670,483 A | 9/1997 | Zhang et al. | |
| 6,362,145 B1 | 3/2002 | Littau et al. | |
| 2012/0014925 A1* | 1/2012 | Kumada | A61L 27/227 424/93.7 |
| 2012/0238039 A1 | 9/2012 | Cha et al. | |

FOREIGN PATENT DOCUMENTS

| | | | |
|---|---|---|---|
| KR | 10-2012-0013626 A | 2/2012 | |
| KR | 10-2012-0075917 A | 7/2012 | |
| KR | 10-2013-0027908 A | 3/2013 | |
| WO | WO-2008150101 A2 * | 12/2008 | ....... C07K 14/43504 |
| WO | 2011/115420 A2 | 9/2011 | |
| WO | WO-2015126480 A2 * | 8/2015 | |

OTHER PUBLICATIONS

Ceylan et al., 'Mussel inspired dynamic cross-linking of self-healing peptide nanofiber network', Advanced Functional Materials, 2013, vol. 23, No. 16, pp. 2081-2090.

* cited by examiner

*Primary Examiner* — James H Alstrum-Acevedo
*Assistant Examiner* — Erinne R Dabkowski
(74) *Attorney, Agent, or Firm* — Vorys, Sater, Seymour & Pease LLP; Mih Suhn Koh

(57) ABSTRACT

Provided herein is a surfactant adhesive protein comprising an amphiphilic peptide at the carbon or amine terminal of the protein, enabling homogeneous dispersion of several materials in various solvents and coating of the homogeneously dispersed particles on a hydrophilic or hydrophobic surface, particularly the homogeneous dispersion of hydrophilic or hydrophobic particles in a hydrophobic or hydrophilic solvent on the basis of strong adhesive strength of a mussel adhesive protein; the surface adhesive protein can be used as a surface coating agent requiring antibacterial or antiviral functions as well as a cosmetic product or an ink.

11 Claims, 2 Drawing Sheets

Specification includes a Sequence Listing.

SEQUENCE LISTING

```
<160> NUMBER OF SEQ ID NOS: 35

<210> SEQ ID NO 1
<211> LENGTH: 10
<212> TYPE: PRT
<213> ORGANISM: Artificial Sequence
<220> FEATURE:
<223> OTHER INFORMATION: model peptide of the tandem repeat decapeptide
      derived from foot protein 1 (FP-1, Mytilus edulis)

<400> SEQUENCE: 1

Ala Lys Pro Ser Tyr Pro Pro Thr Tyr Lys
1               5                   10

<210> SEQ ID NO 2
<211> LENGTH: 20
<212> TYPE: PRT
<213> ORGANISM: Artificial Sequence
<220> FEATURE:
<223> OTHER INFORMATION: 2 times repeated sequence derived from foot
      protein 1 (FP-1, Mytilus edulis)

<400> SEQUENCE: 2

Ala Lys Pro Ser Tyr Pro Pro Thr Tyr Lys Ala Lys Pro Ser Tyr Pro
1               5                   10                  15

Pro Thr Tyr Lys
            20

<210> SEQ ID NO 3
<211> LENGTH: 60
<212> TYPE: PRT
<213> ORGANISM: Artificial Sequence
<220> FEATURE:
<223> OTHER INFORMATION: 6 times repeated sequence derived from foot
      protein 1 (FP-1, Mytilus edulis)

<400> SEQUENCE: 3

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
        35                  40                  45

Tyr Lys Ala Lys Pro Ser Tyr Pro Pro Thr Tyr Lys
    50                  55                  60

<210> SEQ ID NO 4
<211> LENGTH: 39
<212> TYPE: PRT
<213> ORGANISM: Artificial Sequence
<220> FEATURE:
<223> OTHER INFORMATION: partial sequence of foot protein type 2 (FP-2,
      Mytilus californianus)

<400> SEQUENCE: 4

Glu Val His Ala Cys Lys Pro Asn Pro Cys Lys Asn Asn Gly Arg Cys
1               5                   10                  15
```

Tyr Pro Asp Gly Lys Thr Gly Tyr Lys Cys Lys Cys Val Gly Gly Tyr
            20                  25                  30

Ser Gly Pro Thr Cys Ala Cys
        35

<210> SEQ ID NO 5
<211> LENGTH: 52
<212> TYPE: PRT
<213> ORGANISM: Artificial Sequence
<220> FEATURE:
<223> OTHER INFORMATION: Foot protein type 3 (FP-3, Mytilus edulis)

<400> SEQUENCE: 5

Ala Asp Tyr Tyr Gly Pro Lys Tyr Gly Pro Pro Arg Arg Tyr Gly Gly
1               5                   10                  15

Gly Asn Tyr Asn Arg Tyr Gly Gly Ser Arg Arg Tyr Gly Gly Tyr Lys
            20                  25                  30

Gly Trp Asn Asn Gly Trp Lys Arg Gly Arg Trp Gly Arg Lys Tyr Tyr
        35                  40                  45

Glu Phe Glu Phe
    50

<210> SEQ ID NO 6
<211> LENGTH: 46
<212> TYPE: PRT
<213> ORGANISM: Artificial Sequence
<220> FEATURE:
<223> OTHER INFORMATION: Foot protein type 3 (FP-3, Mytilus
      galloprovincialis : mgfp-3A)

<400> SEQUENCE: 6

Ala Asp Tyr Tyr Gly Pro Lys Tyr Gly Pro Pro Arg Arg Tyr Gly Gly
1               5                   10                  15

Gly Asn Tyr Asn Arg Tyr Gly Arg Arg Tyr Gly Gly Tyr Lys Gly Trp
            20                  25                  30

Asn Asn Gly Trp Lys Arg Gly Arg Trp Gly Arg Lys Tyr Tyr
        35                  40                  45

<210> SEQ ID NO 7
<211> LENGTH: 50
<212> TYPE: PRT
<213> ORGANISM: Artificial Sequence
<220> FEATURE:
<223> OTHER INFORMATION: Foot protein type 3 (FP-3, Mytilus edulis:
      mefp-3F)

<400> SEQUENCE: 7

Ala Asp Tyr Tyr Gly Pro Asn Tyr Gly Pro Pro Arg Arg Tyr Gly Gly
1               5                   10                  15

Gly Asn Tyr Asn Arg Tyr Asn Gly Tyr Gly Gly Gly Arg Arg Tyr Gly
            20                  25                  30

Gly Tyr Lys Gly Trp Asn Asn Gly Trp Asn Arg Gly Arg Arg Gly Lys
        35                  40                  45

Tyr Trp
    50

<210> SEQ ID NO 8
<211> LENGTH: 44
<212> TYPE: PRT
<213> ORGANISM: Artificial Sequence
<220> FEATURE:
<223> OTHER INFORMATION: Foot protein type 3 (FP-3, Mytilus
      californianus)

-continued

```
<400> SEQUENCE: 8

Gly Ala Tyr Lys Gly Pro Asn Tyr Asn Tyr Pro Trp Arg Tyr Gly Gly
1               5                   10                  15

Lys Tyr Asn Gly Tyr Lys Gly Tyr Pro Arg Gly Tyr Gly Trp Asn Lys
            20                  25                  30

Gly Trp Asn Lys Gly Arg Trp Gly Arg Lys Tyr Tyr
            35                  40

<210> SEQ ID NO 9
<211> LENGTH: 60
<212> TYPE: PRT
<213> ORGANISM: Artificial Sequence
<220> FEATURE:
<223> OTHER INFORMATION: partial sequence from foot protein type 4
      (Mytilus californianus)

<400> SEQUENCE: 9

Gly His Val His Arg His Arg Val Leu His Lys His Val His Asn His
1               5                   10                  15

Arg Val Leu His Lys His Leu His Lys His Gln Val Leu His Gly His
            20                  25                  30

Val His Arg His Gln Val Leu His Lys His Val His Asn His Arg Val
        35                  40                  45

Leu His Lys His Leu His Lys His Gln Val Leu His
    50                  55                  60

<210> SEQ ID NO 10
<211> LENGTH: 75
<212> TYPE: PRT
<213> ORGANISM: Artificial Sequence
<220> FEATURE:
<223> OTHER INFORMATION: Foot protein type5 (FP-5, Mytilus edulis)

<400> SEQUENCE: 10

Ser Ser Glu Glu Tyr Lys Gly Gly Tyr Tyr Pro Gly Asn Ala Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Ser Ser
65                  70                  75

<210> SEQ ID NO 11
<211> LENGTH: 76
<212> TYPE: PRT
<213> ORGANISM: Artificial Sequence
<220> FEATURE:
<223> OTHER INFORMATION: Foot protein 5 (FP-5, Mytilus edulis)

<400> SEQUENCE: 11

Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45
```

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Ser Ser
65                  70                  75

<210> SEQ ID NO 12
<211> LENGTH: 71
<212> TYPE: PRT
<213> ORGANISM: Artificial Sequence
<220> FEATURE:
<223> OTHER INFORMATION: Foot protein 5 (FP-5, Mytilus coruscus)

<400> SEQUENCE: 12

Tyr Asp Asp Tyr Ser Asp Gly Tyr Tyr Pro Gly Ser Ala Tyr Asn Tyr
1               5                   10                  15

Pro Ser Gly Ser His Trp His Gly His Gly Tyr Lys Gly Lys Tyr Tyr
            20                  25                  30

Gly Lys Gly Lys Lys Tyr Tyr Tyr Lys Phe Lys Arg Thr Gly Lys Tyr
        35                  40                  45

Lys Tyr Leu Lys Lys Ala Arg Lys Tyr His Arg Lys Gly Tyr Lys Lys
    50                  55                  60

His Tyr Gly Gly Ser Ser Ser
65                  70

<210> SEQ ID NO 13
<211> LENGTH: 76
<212> TYPE: PRT
<213> ORGANISM: Artificial Sequence
<220> FEATURE:
<223> OTHER INFORMATION: mussel adhesive protein foot protein type5 from
      (Mytilus galloprovincialis)

<400> SEQUENCE: 13

Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Ser Ser
65                  70                  75

<210> SEQ ID NO 14
<211> LENGTH: 99
<212> TYPE: PRT
<213> ORGANISM: Artificial Sequence
<220> FEATURE:
<223> OTHER INFORMATION: mussel adhesive protein foot protein type 6

<400> SEQUENCE: 14

Gly Gly Gly Asn Tyr Arg Gly Tyr Cys Ser Asn Lys Gly Cys Arg Ser
1               5                   10                  15

Gly Tyr Ile Phe Tyr Asp Asn Arg Gly Phe Cys Lys Tyr Gly Ser Ser
            20                  25                  30

Ser Tyr Lys Tyr Asp Cys Gly Asn Tyr Ala Gly Cys Cys Leu Pro Arg
        35                  40                  45

Asn Pro Tyr Gly Arg Val Lys Tyr Tyr Cys Thr Lys Lys Tyr Ser Cys
    50                  55                  60

Pro Asp Asp Phe Tyr Tyr Asn Asn Lys Gly Tyr Tyr Tyr Asn
65                  70                  75                  80

Asp Lys Asp Tyr Phe Asn Cys Gly Ser Tyr Asn Gly Cys Cys Leu Arg
            85                  90                  95

Ser Gly Tyr

<210> SEQ ID NO 15
<211> LENGTH: 194
<212> TYPE: PRT
<213> ORGANISM: Artificial Sequence
<220> FEATURE:
<223> OTHER INFORMATION: hybrid mussel adhesive protein (FP-151, MEFP-5 based)

<400> SEQUENCE: 15

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
            35                  40                  45

Tyr Lys Ala Lys Pro Ser Tyr Pro Pro Thr Tyr Lys Ser Ser Glu Glu
50                  55                  60

Tyr Lys Gly Gly Tyr Tyr Pro Gly Asn Ala Tyr His Tyr His Ser Gly
65                  70                  75                  80

Gly Ser Tyr His Gly Ser Gly Tyr His Gly Gly Tyr Lys Gly Lys Tyr
            85                  90                  95

Tyr Gly Lys Ala Lys Lys Tyr Tyr Tyr Lys Tyr Lys Asn Ser Gly Lys
            100                 105                 110

Tyr Lys Tyr Leu Lys Lys Ala Arg Lys Tyr His Arg Lys Gly Tyr Lys
            115                 120                 125

Tyr Tyr Gly Gly Ser Ser Ala Lys Pro Ser Tyr Pro Pro Thr Tyr Lys
130                 135                 140

Ala Lys Pro Ser Tyr Pro Pro Thr Tyr Lys Ala Lys Pro Ser Tyr Pro
145                 150                 155                 160

Pro Thr Tyr Lys Ala Lys Pro Ser Tyr Pro Pro Thr Tyr Lys Ala Lys
            165                 170                 175

Pro Ser Tyr Pro Pro Thr Tyr Lys Ala Lys Pro Ser Tyr Pro Pro Thr
            180                 185                 190

Tyr Lys

<210> SEQ ID NO 16
<211> LENGTH: 196
<212> TYPE: PRT
<213> ORGANISM: Artificial Sequence
<220> FEATURE:
<223> OTHER INFORMATION: hybrid mussel adhesive protein (FP-151, MGFP-5 based)

<400> SEQUENCE: 16

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
            35                  40                  45

Tyr Lys Ala Lys Pro Ser Tyr Pro Pro Thr Tyr Lys Ser Ser Glu Glu
50                  55                  60

```
Tyr Lys Gly Gly Tyr Tyr Pro Gly Asn Thr Tyr His Tyr His Ser Gly
 65                  70                  75                  80

Gly Ser Tyr His Gly Ser Gly Tyr His Gly Gly Tyr Lys Gly Lys Tyr
             85                  90                  95

Tyr Gly Lys Ala Lys Lys Tyr Tyr Lys Tyr Lys Asn Ser Gly Lys
        100                 105                 110

Tyr Lys Tyr Leu Lys Lys Ala Arg Lys Tyr His Arg Lys Gly Tyr Lys
        115                 120                 125

Lys Tyr Tyr Gly Gly Gly Ser Ser Ala Lys Pro Ser Tyr Pro Pro Thr
130                 135                 140

Tyr Lys Ala Lys Pro Ser Tyr Pro Pro Thr Tyr Lys Ala Lys Pro Ser
145                 150                 155                 160

Tyr Pro Pro Thr Tyr Lys Ala Lys Pro Ser Tyr Pro Pro Thr Tyr Lys
                165                 170                 175

Ala Lys Pro Ser Tyr Pro Pro Thr Tyr Lys Ala Lys Pro Ser Tyr Pro
                180                 185                 190

Pro Thr Tyr Lys
            195
```

<210> SEQ ID NO 17
<211> LENGTH: 192
<212> TYPE: PRT
<213> ORGANISM: Artificial Sequence
<220> FEATURE:
<223> OTHER INFORMATION: hybrid mussel adhesive protein (FP-151, MCFP-5 based)

<400> SEQUENCE: 17

```
Ala Lys Pro Ser Tyr Pro Pro Thr Tyr Lys Ala Lys Pro Ser Tyr Pro
  1               5                  10                  15

Pro Thr Tyr Lys Ala Lys Pro Ser Tyr Pro Pro Thr Tyr Lys Ala Lys
             20                  25                  30

Pro Ser Tyr Pro Pro Thr Tyr Lys Ala Lys Pro Ser Tyr Pro Pro Thr
         35                  40                  45

Tyr Lys Ala Lys Pro Ser Tyr Pro Pro Thr Tyr Lys Tyr Asp Gly Tyr
 50                  55                  60

Ser Asp Gly Tyr Tyr Pro Gly Ser Ala Tyr Asn Tyr Pro Ser Gly Ser
 65                  70                  75                  80

His Gly Tyr His Gly His Gly Tyr Lys Gly Lys Tyr Gly Lys Gly
             85                  90                  95

Lys Lys Tyr Tyr Lys Tyr Lys Arg Thr Gly Lys Tyr Lys Tyr Leu
        100                 105                 110

Lys Lys Ala Arg Lys Tyr His Arg Lys Gly Tyr Lys Lys Tyr Tyr Gly
115                 120                 125

Gly Gly Ser Ser Ala Lys Pro Ser Tyr Pro Pro Thr Tyr Lys Ala Lys
130                 135                 140

Pro Ser Tyr Pro Pro Thr Tyr Lys Ala Lys Pro Ser Tyr Pro Pro Thr
145                 150                 155                 160

Tyr Lys Ala Lys Pro Ser Tyr Pro Pro Thr Tyr Lys Ala Lys Pro Ser
                165                 170                 175

Tyr Pro Pro Thr Tyr Lys Ala Lys Pro Ser Tyr Pro Pro Thr Tyr Lys
                180                 185                 190
```

<210> SEQ ID NO 18
<211> LENGTH: 177
<212> TYPE: PRT

<213> ORGANISM: Artificial Sequence
<220> FEATURE:
<223> OTHER INFORMATION: hybrid mussel adhesive protein (FP-131)

<400> SEQUENCE: 18

```
Ala Lys Pro Ser Tyr Pro Pro Thr Tyr Lys Ala Lys Pro Ser Tyr Pro
1               5                   10                  15
Pro Thr Tyr Lys Ala Lys Pro Ser Tyr Pro Pro Thr Tyr Lys Ala Lys
            20                  25                  30
Pro Ser Tyr Pro Pro Thr Tyr Lys Ala Lys Pro Ser Tyr Pro Pro Thr
        35                  40                  45
Tyr Lys Ala Lys Pro Ser Tyr Pro Pro Thr Tyr Lys Gly Cys Arg Ala
50                  55                  60
Asp Tyr Tyr Gly Pro Lys Tyr Gly Pro Pro Arg Arg Tyr Gly Gly Gly
65                  70                  75                  80
Asn Tyr Asn Arg Tyr Gly Gly Ser Arg Arg Tyr Gly Gly Tyr Lys Gly
                85                  90                  95
Trp Asn Asn Gly Trp Lys Arg Gly Arg Trp Gly Arg Lys Tyr Tyr Glu
                100                 105                 110
Phe Glu Phe Ala Lys Pro Ser Tyr Pro Pro Thr Tyr Lys Ala Lys Pro
            115                 120                 125
Ser Tyr Pro Pro Thr Tyr Lys Ala Lys Pro Ser Tyr Pro Pro Thr Tyr
        130                 135                 140
Lys Ala Lys Pro Ser Tyr Pro Pro Thr Tyr Lys Ala Lys Pro Ser Tyr
145                 150                 155                 160
Pro Pro Thr Tyr Lys Ala Lys Pro Ser Tyr Pro Pro Thr Tyr Lys Lys
                165                 170                 175
Leu
```

<210> SEQ ID NO 19
<211> LENGTH: 180
<212> TYPE: PRT
<213> ORGANISM: Artificial Sequence
<220> FEATURE:
<223> OTHER INFORMATION: hybrid mussel adhesive protein (FP-251)

<400> SEQUENCE: 19

```
Met Glu Val His Ala Cys Lys Pro Asn Pro Cys Lys Asn Asn Gly Arg
1               5                   10                  15
Cys Tyr Pro Asp Gly Lys Thr Gly Tyr Lys Cys Lys Cys Val Gly Gly
            20                  25                  30
Tyr Ser Gly Pro Thr Cys Ala Cys Ser Ser Glu Glu Tyr Lys Gly Gly
        35                  40                  45
Tyr Tyr Pro Gly Asn Ser Asn His Tyr His Ser Gly Ser Tyr His
50                  55                  60
Gly Ser Gly Tyr His Gly Gly Tyr Lys Gly Lys Tyr Tyr Gly Lys Ala
65                  70                  75                  80
Lys Lys Tyr Tyr Tyr Lys Tyr Lys Asn Ser Gly Lys Tyr Lys Tyr Leu
                85                  90                  95
Lys Lys Ala Arg Lys Tyr His Arg Lys Gly Tyr Lys Lys Tyr Tyr Gly
                100                 105                 110
Gly Ser Ser Glu Phe Glu Phe Ala Lys Pro Ser Tyr Pro Pro Thr Tyr
            115                 120                 125
Lys Ala Lys Pro Ser Tyr Pro Pro Thr Tyr Lys Ala Lys Pro Ser Tyr
        130                 135                 140
Pro Pro Thr Tyr Lys Ala Lys Pro Ser Tyr Pro Pro Thr Tyr Lys Ala
```

```
              145                 150                 155                 160
Lys Pro Ser Tyr Pro Pro Thr Tyr Lys Ala Lys Pro Ser Tyr Pro Pro
                165                 170                 175
Thr Tyr Lys Lys
            180

<210> SEQ ID NO 20
<211> LENGTH: 16
<212> TYPE: PRT
<213> ORGANISM: Artificial Sequence
<220> FEATURE:
<223> OTHER INFORMATION: Amphiphilic peptide (ARARADADARARADAD)

<400> SEQUENCE: 20

Ala Arg Ala Arg Ala Asp Ala Asp Ala Arg Ala Arg Ala Asp Ala Asp
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Amphiphilic peptide (EAEAKAKAEAEAKAKA)

<400> SEQUENCE: 21

Glu Ala Glu Ala Lys Ala Lys Ala Glu Ala Glu Ala Lys Ala Lys Ala
1               5                   10                  15

<210> SEQ ID NO 22
<211> LENGTH: 11
<212> TYPE: PRT
<213> ORGANISM: Artificial Sequence
<220> FEATURE:
<223> OTHER INFORMATION: Amphiphilic peptide (QQRFQWQFEQQ)

<400> SEQUENCE: 22

Gln Gln Arg Phe Gln Trp Gln Phe Glu Gln Gln
1               5                   10

<210> SEQ ID NO 23
<211> LENGTH: 8
<212> TYPE: PRT
<213> ORGANISM: Artificial Sequence
<220> FEATURE:
<223> OTHER INFORMATION: Amphiphilic peptide (AEAEAKAK)

<400> SEQUENCE: 23

Ala Glu Ala Glu Ala Lys Ala Lys
1               5

<210> SEQ ID NO 24
<211> LENGTH: 12
<212> TYPE: PRT
<213> ORGANISM: Artificial Sequence
<220> FEATURE:
<223> OTHER INFORMATION: CNT binding peptide (DPHHHWYHMHQH)

<400> SEQUENCE: 24

Asp Pro His His His Trp Tyr His Met His Gln His
1               5                   10

<210> SEQ ID NO 25
<211> LENGTH: 12
<212> TYPE: PRT
<213> ORGANISM: Artificial Sequence
<220> FEATURE:
```

```
<223> OTHER INFORMATION: CNT binding peptide (HNWYHWWMPHNT)

<400> SEQUENCE: 25

His Asn Trp Tyr His Trp Trp Met Pro His Asn Thr
1               5                   10

<210> SEQ ID NO 26
<211> LENGTH: 12
<212> TYPE: PRT
<213> ORGANISM: Artificial Sequence
<220> FEATURE:
<223> OTHER INFORMATION: CNT binding peptide (HWKHPWGAWDTL)

<400> SEQUENCE: 26

His Trp Lys His Pro Trp Gly Ala Trp Asp Thr Leu
1               5                   10

<210> SEQ ID NO 27
<211> LENGTH: 12
<212> TYPE: PRT
<213> ORGANISM: Artificial Sequence
<220> FEATURE:
<223> OTHER INFORMATION: CNT binding peptide (HWSAWWIRSNQS)

<400> SEQUENCE: 27

His Trp Ser Ala Trp Trp Ile Arg Ser Asn Gln Ser
1               5                   10

<210> SEQ ID NO 28
<211> LENGTH: 12
<212> TYPE: PRT
<213> ORGANISM: Artificial Sequence
<220> FEATURE:
<223> OTHER INFORMATION: CNT binding peptide (DDWSHWWRAWNG)

<400> SEQUENCE: 28

Asp Asp Trp Ser His Trp Trp Arg Ala Trp Asn Gly
1               5                   10

<210> SEQ ID NO 29
<211> LENGTH: 12
<212> TYPE: PRT
<213> ORGANISM: Artificial Sequence
<220> FEATURE:
<223> OTHER INFORMATION: CNT binding peptide (YTSPWWLAWYDP)

<400> SEQUENCE: 29

Tyr Thr Ser Pro Trp Trp Leu Ala Trp Tyr Asp Pro
1               5                   10

<210> SEQ ID NO 30
<211> LENGTH: 12
<212> TYPE: PRT
<213> ORGANISM: Artificial Sequence
<220> FEATURE:
<223> OTHER INFORMATION: CNT binding peptide (AWWEAFIPNSIT)

<400> SEQUENCE: 30

Ala Trp Trp Glu Ala Phe Ile Pro Asn Ser Ile Thr
1               5                   10

<210> SEQ ID NO 31
<211> LENGTH: 16
<212> TYPE: PRT
<213> ORGANISM: Artificial Sequence
<220> FEATURE:
<223> OTHER INFORMATION: Anti-microbacterial peptide (KLWKKWAKKWLKLWKA)
```

```
<400> SEQUENCE: 31

Lys Leu Trp Lys Lys Trp Ala Lys Lys Trp Leu Lys Leu Trp Lys Ala
1               5                   10                  15

<210> SEQ ID NO 32
<211> LENGTH: 11
<212> TYPE: PRT
<213> ORGANISM: Artificial Sequence
<220> FEATURE:
<223> OTHER INFORMATION: Anti-microbacterial peptide (FALALKALKKL)

<400> SEQUENCE: 32

Phe Ala Leu Ala Leu Lys Ala Leu Lys Lys Leu
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Anti-microbacterial peptide (ILRWPWWPWRRK)

<400> SEQUENCE: 33

Ile Leu Arg Trp Pro Trp Trp Pro Trp Arg Arg Lys
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Anti-microbacterial peptide (AKRHHGYKRKFH)

<400> SEQUENCE: 34

Ala Lys Arg His His Gly Tyr Lys Arg Lys Phe His
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Anti-viral peptide (RRWWCRC)

<400> SEQUENCE: 35

Arg Arg Trp Trp Cys Arg Cys
1               5
```

SURFACTANT ADHESIVE COMPOSITION

SEQUENCE LISTING

The Sequence Listing submitted in text format (.txt) filed on Jul. 3, 2018, named "SequenceListing.txt", created on Jul. 3, 2018 (21.1 KB), is incorporated herein by reference.

FIELD OF INVENTION

The present invention relates to a biofunctional adhesive with surfactant activity, and a method of preparing said biofunctional adhesive surfactant. In details, the present invention related to an adhesive composition, comprising amphiphilic peptide recombinantly incorporated into the molecular backbone of an adhesive protein. Said adhesive protein of the present invention is an adhesive protein having antimicrobial, antiviral or anti-atopic peptide recombinantly incorporated into C-terminal or N-terminal of said adhesive protein.

BACKGROUND OF THE INVENTION

A surfactant is the chemical compound composed of hydrophilic domain and hydrophobic domain in the same molecule, and is used in most industries including advanced industry such as medicine, nanomaterial and fine chemicals. A lot of surfactants are used in commodities.

A surfactant reducing interfacial tension offers excellent detergent, dispersion, emulsification, solubilizing agent, and antimicrobial effect and is used in industrial detergent as well as household detergent. U.S. Pat. No. 6,362,145 discloses a method of manufacturing excellent detergent comprising SLES (sodium lauryl ether sulfate). U.S. Pat. Nos. 5,368,756 and 5,230,823 describe a method of manufacturing ionic surfactant, for example, cationic quaternary ammonium based surfactant.

These surfactants have small molecular weight enough to absorb transdermally when contacted with skin. Some petroleum-based sulfate surfactants were not excreted or eliminated from the body but accumulated in the human body, causing skin cancer or atopic symptoms. Especially, many reports of side effect related to atopic dermatitis or other symptoms caused by anionic surfactant SLS (sodium lauryl sulfate), sodium lauryl ether sulfate (SLES) and ammonium lauryl Sulfate (ALS) have been made continuously.

Naturally occurring surfactants, such as lecithin, extracted from plants have been developed. For example, Korean patent publication No. 10-2013-0027908 discloses a method of manufacturing surfactant composition comprising mung bean saponin and alkyl glucoside sulfonate, a mild detergent and little sensitive to skin. The natural surfactants are human body- or environment-friendly, but its high cost structure prohibits extensive industrial applications.

The present invention discloses a method of manufacturing adhesive protein having surfactant activity in order to address the issues described above and to provide human body- and environment-friendly surfactant protein. In one embodiment of the present invention, provided is a surfactant adhesive protein whose molecular backbone is amphiphilic, without any special equipment or treatment, simply used as an additive. Furthermore, the surfactant adhesive can be used as water-soluble or oil-soluble coating material.

DETAILED DESCRIPTION OF THE INVENTION

The present invention is designed to address the issues described above. According to one embodiment of the present invention, the objective of the invention is to provide interfacially active adhesive protein, i.e. surfactant adhesive protein, based material or coating composition with excellent affinity to hydrophilic or lyophilic surface. Furthermore, another objective of the invention is to develop an adhesive protein fused with a variety of functional peptides such as antimicrobial, anti-atopic, antiviral peptide fused at C-terminus or N-terminus of said adhesive protein, and a coating or adhesive composition comprising the same. The functional peptide of the present invention refers to any peptide composed of three or more amino acid residues with physiological function such as antimicrobial, anticancer, anti-immune, antiviral, anti-atopic, anti-thrombotic activity. According to another embodiment of the present invention, another objective of the invention is to provide a simple coating method by adjusting of the concentration of mussel adhesive protein, and coating composition wherein said coating composition is environment-friendly coating materials without use of organic solvent by providing water-soluble or oil-soluble, and endurable coating composition.

Another objective of the present invention is to provide human body friendly surfactant materials for various commodity applications such as cosmetics.

It should be obviously understood that special advantages and novel features of the present invention by drawings and its related illustrated embodiments in the present invention.

The present invention relates to amphiphilic adhesive protein having high affinity to water-soluble or oil-soluble solvent and provides said adhesive protein based adhesive or coating composition.

The present invention further provides an adhesive protein with excellent surfactant activity by recombinantly incorporating amphiphilic peptide into C-terminus or N-terminus of an adhesive protein.

According to one embodiment of the present invention, provided is an interfacially active adhesive protein with antimicrobial activity by incorporating amphiphilic peptide into antimicrobial adhesive protein which is finely and stably dispersed in silicone oil or olive oil used for cosmetic purpose.

The present invention provides a surfactant adhesive protein having amphiphilic properties as a surface active agent. The surface active agent in the present invention is composed of adhesive protein functionalized with naturally occurring or synthetically designed amphiphilic peptides, wherein the basic structure of the adhesive protein has formula (X-Y-A) or (X-A-Y), wherein X is an domain containing hydrophobic peptide, Y is an domain containing hydrophilic peptide, and A is an amphiphilic peptide containing domain.

Any suitable adhesive protein may be used as the surfactant adhesive materials of the present invention.

The adhesive protein used in the present invention includes, but not limited to, a self-adhesive protein. Self-adhesive protein possesses adhesiveness inherently or by chemical modification. One example of commerically available said self-adhesive protein includes, but not limited to a mussel-derived recombinant adhesive protein, MAPTRIX™ (Mussel Adhesive Protein based Matrix) marketed by Kollodis BioSciences Inc. (North Augusta, Mass.). Another example of said self-adhesive protein through chemical modification is an acrylated adhesive protein. For example, acrylated collagen or mussel adhesive protein is self-adhesive. One embodiment of the present invention provides a surfactant adhesive protein comprising mussel adhesive protein.

MAPTRIX™ (Mussel Adhesive Protein based Matrix) disclosed in the present invention is a recombinantly functionalized mussel adhesive protein. Y domain, the hydrophilic peptide domain, in the present invention may comprises foot protein 5 (FP-5) selected from SEQ ID NO. 10, 11, 12 or 13, foot protein 3 (FP-3) selected from SEQ ID NO. 5, 6, 7 or 8, or foot protein 6 (FP-6) comprising SEQ ID NO. 14, wherein C-terminus, N-terminus or C- and N-terminus of Y domain is fused with domain X, selected from relatively hydrophobic mussel adhesive protein FP-1 (SEQ ID NO. 1), FP-2 (SEQ ID NO. 4), FP-4 (SEQ ID NO. 9) or its fragment. Preferably, said X domain may comprise FP-5 selected from amino acid sequences SEQ ID NO. 10, 11, 12 or 13 and said Y domain may comprise FP-1 selected from amino acid sequences SEQ ID NO. 1, 2 or 3. A domain in the present invention is necessary for said fused mussel adhesive protein to have surface-active function by maximizing a contact area in various solvents or surfaces.

The amphiphilic peptide described above may be recombinantly incorporated into C-, N-terminus, or both N- and C-termini of mussel adhesive protein, or between one domain and another domain of fused mussel adhesive protein. For example, any amphiphilic peptide can be recombinantly incorporated into between FP-1 and FP-5 of a fused protein FP-151 (FP-5 domain fused with FP1). In addition, a bioactive peptide such as antimicrobial or anti-viral peptide may be incorporated into both N- and C-terminus or between domains of a fused protein. For example, such bioactive peptide may include Magainin, alpha-helical 23-amino acid peptide forming isolated from the skin of the African clawed frog *Xenopus laevis* or Dermaseptin antimicrobial peptide. Furthermore, human defensins, cathelicidin LL-37, histatin antimicrobial peptide may be included but not limited to such antimicrobial peptide. According to a preferable embodiment of the present invention, the fusion protein may be used, but not limited to, FP-151 having amino acid sequence of SEQ ID NOs. 15-17, FP-131 having amino acid sequence of SEQ ID NO. 18, or FP-251 having amino acid sequence of SEQ ID NO. 19.

The present invention provides an amphiphilic peptide fused with said adhesive protein wherein said amphiphilic peptide is naturally occurring or synthetically designed. Generally, an amphiphilic peptide has good solubility in both hydrophilic and hydrophobic solvent. Any amphiphilic peptide comprising alternating pattern of hydrophobic-hydrophilic amino acid or hydrophobic-hydrophilic block amino acid may be used in the present invention. Preferably, said amphiphilic peptide incorporated into said adhesive protein may be selected from synthetically designed peptides. More preferably, said amphiphilic peptide may be selected from ARARADADARARADAD (SEQ ID NO. 20), EAEAKAKAEAEAKAKA (SEQ ID NO. 21), QQRFQWQFEQQ (SEQ ID NO. 22), AEAEAKAK (SEQ ID NO. 23), DPHHHWYHMHQH (SEQ ID NO. 24), HNWYHWWMPHNT (SEQ ID NO. 25), HWKHPWGAWDTL (SEQ ID NO. 26), HWSAWWIRSNQS (SEQ ID NO. 27), DDWSHWWRAWNG (SEQ ID NO. 28), YTSPWWLAWYDP (SEQ ID NO. 29), AWWEAFIPNSIT (SEQ ID NO. 30) and KLWKKWAKKWLKLWKA (SEQ ID NO. 31).

Biofunctional adhesives provided in the present invention may include anti-viral or antimicrobial peptide. Antimicrobial or antiviral surfactant adhesives may include naturally occurring or synthetically designed peptide. Preferably, the peptide may be selected from antimicrobial peptide FALALKALKKL (SEQ ID NO. 32), ILRWPWWPWRRK (SEQ ID NO. 33), AKRHHGYKRKFH (SEQ ID NO. 34), or antiviral peptide RRWWCRC (SEQ ID NO. 35).

In order to provide adhesive protein with good surfactant activity in a wide variety of solvents, provided is an antimicrobial adhesive protein based surfactant wherein two different amphiphilic peptides are incorporated into C-terminus and N-terminus of said antimicrobial adhesive protein, respectively. A broad range of interfacially active coating composition is provided in the present invention wherein said interfacially active coating composition comprises adhesive protein having one amphiphilic peptide EAEAKAKAEAEAKAKA (SEQ ID NO. 21) fused at the N-terminus, and another amphiphilic peptide QQRFQWQFEQQ (SEQ ID NO. 22) fused at C-terminus of said adhesive protein.

The tyrosine residues in the fused mussel adhesive protein may be modified to DOPA (3,4-dihydroxyphenylalanine), further oxidative conversion to DOPA-quinone, and the modified forms of DOPA and DOPA-quinone are known to play an important role in surface adhesion. Chemical modification of recombinant mussel adhesive protein can be conducted with tyrosinase from mushroom, catalyzing such modification. The surfactant mussel adhesive protein chemically modified with tyrosinase may disperse, finely and stably, a variety of materials including carbon nanotube, metals, plastics, glass, ceramics in hydrophilic or hydrophobic solvent.

The concentration of coating composition based on surfactant adhesive protein can be adjusted depending on the concentration of amphiphilic peptide fused with said adhesive protein. Preferably, the concentration of surfactant adhesive protein based coating composition is 0.1 to 10% (wt/wt), more preferably, 0.1 to 3% (wt/wt).

In one embodiment of the present invention, provided is solution of mica particles treated with surfactant adhesive protein were finely dispersed in silicone oil and the present inventors confirmed the adhesiveness of surfactant adhesive protein by immobilizing surfactant adhesive protein treated-mica particles which were dispersed in silicon oil to wet surface.

Advantageous Effects

The present invention of adhesive protein with surface active characteristics may enables fine dispersion of various materials in a variety of solvents, and the finely dispersed particles may be coated to hydrophilic or hydrophobic surface. Particularly, mussel adhesive protein with strong adhesion in the present invention enables fine dispersion of hydrophilic or hydrophobic particles in hydrophobic or hydrophilic solvent, the invention can be applied to cosmetics, inks or functional surface coating agent requiring antimicrobial or antiviral activity.

EXAMPLES

Figure 1:
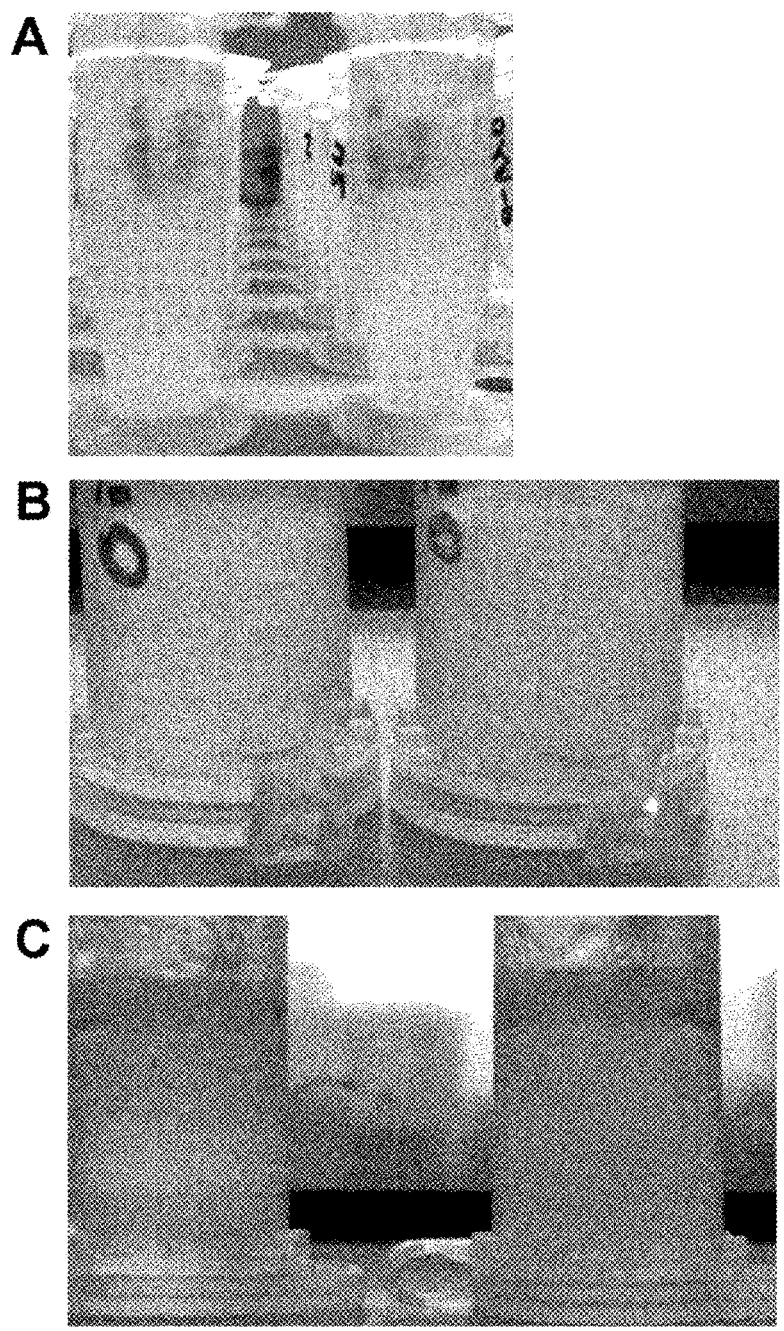
FIG. 1 illustrates mica particles stably and finely dispersed by interfacially active adhesive protein in the mixture of water and silicone oil, demonstrating stable and finely dispersed phase in the mixture of water/silicone oil solution at least five hours. (A) indicates the solution of water and oil at the time of mixture, (B) indicates the solution after one hour, and (C) indicates the solution after five hours.

The following examples are provided to illustrate desirable embodiment purpose in the present invention, and the exemplified embodiments are illustrative only and do not limit the scope of the invention. As exemplified in the following embodiment, it is very clear that functionally same products, composition and methods are included in the present invention.

Example 1. Construction of Vector for Interfacially Active Mussel Adhesive Protein To prepare mussel adhesive protein fused with amphiphilic peptide, we design a genetic sequence to incorporate typical amphiphilic peptide at C terminus or N-terminus of mussel adhesive protein, and the genetic sequence was synthesized by Cosmogentec Co. Ltd. (Seoul, Korea). The constructed vector was transformed into *E. coli* BL21 (DE3), and the fused amphiphilic peptides were listed in Table 1.

TABLE 1

| Fusion peptide | Amphiphilic Peptide Sequence | Fusion site at mussel adhesive protein |
|---|---|---|
| A | ARARADADARARADAD (SEQ ID NO. 20) | C terminus |
| B | EAEAKAKAEAEAKAKA (SEQ ID NO. 21) | N terminus |
| C | HWKHPWGAWDTL (SEQ ID NO. 22) | C terminus |

Example 2. Preparation of Surfactant Mussel Adhesive Protein 2.1. Culturing of *E. coli* BL21(DE3)

*E. coli* BL21 (DE) was cultured in LB media (5 g/liter yeast extract, 10 g/liter Tryptone and 10 g/liter NaCl), and IPTG was added to a final concentration of 1 mM when the optical density of the culture solution was 0.6 at 600 nm in order to induce expression of recombinantly antimicrobial peptide fused mussel adhesive protein. The *E. coil* BL21 (DE) culture was centrifuged at 13,000 rpm for 4 to 10 minutes to obtain the cell pellet, and this was stored at −80° C.

2.2. Confirmation of Surfactant Mussel Adhesive Protein Expression

The cell pellet was resuspended in 100 µg of SDS-PAGE buffer (0.5 M Tris-HCl, pH 6.8, 10% glycerol, 5% SDS, 5% (3-mercaptoethanol, 0.25% bromophenol blue), denatured by boiling at 100° C. for 5 minutes. For SDS-PAGE analysis, the samples were electrophoresed on a 15% SDS-polyacylamide gel and then the protein bands detected using Coomassie blue staining, 2.3. Purification of Surfactant Mussel Adhesive Protein The cell pellets from EXAMPLE 2.1 was stirred with lysis buffer comprising 2.4 g/L Sodium phosphate monobasic, 5.6 g/L Sodium phosphate dibasic, 10 mM EDTA and 1% Triton X-100, and were broken using high pressure homogenizer. The lysates were centrifuged by centrifugal filter units as 9,000 rpm for 20 minutes and insoluble protein complex containing mussel adhesive protein was obtained. Surfactant adhesive protein eluted from the insoluble complex at an acetic acid concentration of 25 (v/v) % was centrifuged under the same conditions (9,000 rpm for 20 minutes) to gain supernatant. The obtained supernatant was centrifuged under the same conditions (9,000 rpm for 20 minutes) at pH 12.8 by adding 10N NaOH. The supernatant was neutralized at pH 6~7 using acetic acid and then centrifuged under the same conditions to take precipitated mussel adhesive protein. The precipitate was dissolved in distilled water, undergoing freezing-dried to get lyophilized mussel adhesive protein with 90% purity.

Example 3. Treatment of Tyrosinase to the Surfactant Adhesive Protein

The lyophilized surfactant mussel adhesive protein was dissolved to a concentration of 1 mg/mL in 0.1M acetate buffer containing 20 mM ascorbic acid and 20 mM sodium borate and the surfactant adhesive protein solution then saturated with oxygen by adding oxygen gas to the solution for 30 minutes. Then after the addition of 40~1 µg of tyrosinase per antimicrobial adhesive protein, preferably 40~1 µg per adhesive protein, it was shaken for one hour under the oxygen condition. After one hour, the chemical modification reaction was terminated by adding 5% acetic acid to the solution. The terminated surfactant adhesive protein solution underwent freezing dry to obtain lyophilized powder. Through this process, the tyrosine residues of the adhesive proteins were modified to DOPA. After the dialysis of the solution, acrylation and the degree of acrylation of protein were determined with NMR or spectroscopic analysis.

Example 4. Dispersibility Test of Surfactant Protein

Coating solution of surfactant mussel adhesive protein obtained from EXAMPLE 2 was prepared to measure its dispersibility.

The surfactant coating solution was composed of surfactant adhesive protein dissolved to a concentration of 10 to 0.01 mg/mL in distilled water. 2 wt % of Mica particles was added to the surfactant coating solution, and 1 mL of silicone oil was added to the surfactant coating solution. As shown in FIG. 1A, when silicone oil was added to the surfactant coating solution, two phases are separated clearly. Two solutions were mixed using vortex mixer, and mixture and dispersion status of two solutions was checked after 1 and 5 hours. No phase separation of the mixture solution was confirmed after 1 and 5 hours later. Mica particles were finely dispersed and no precipitation of the mica particles was observed, confirming the dispersed phase was stabilized.

Figure 2:
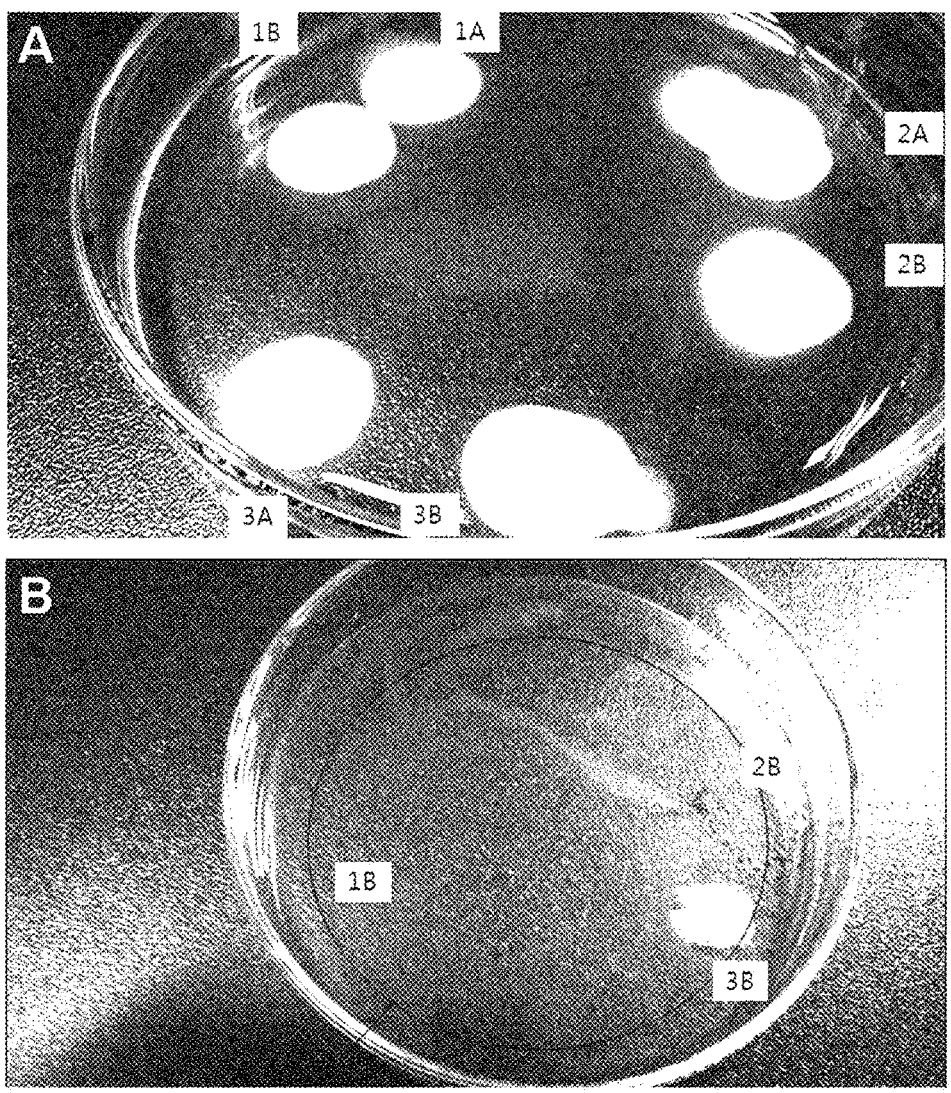
FIG. 2 illustrates the coatability test results of mica particles dispersed in silicone oil to wet surface. When surfactant adhesive protein treated mica particles were dispersed in silicone oil, the mica particles coated with silicone oil showed excellent adhesiveness to wet surface by surface-active effect.

Example 5. Coatability Test with Surfactant Adhesive Protein 0.1 g of mica particles was added to 1 mg, 10 mg and 20 mg of surfactant adhesive protein dissolved in solution, respectively and incubated for 20 minutes for coating. The surfactant adhesive protein coated mica particles were isolated using manure paper and finely dispersed in 1 mL of silicone oil in petri dish. The mica particles finely dispersed silicone oil was added to wet surface coating. FIG. 2A indicated surface coating using surfactant adhesive protein, non-tyrosinase treatment, and FIG. 2B indicated the coating using said adhesive protein was tyrosinase-treated. In FIG. 2A, 1A indicated the mica coated with 1 mg of surfactant adhesive protein, 2A with 10 mg and 3A with 20 mg of surfactant adhesive protein, respectively.

Cotability test was conducted by adding 100 mL of water to mica-coated surface and moving petri dish up and down to exert external stress to coated surface. As shown in FIG. 2B, 3B indicates stable coating, 2B indicates residual coated particles are rare, but 1B indicates little residual coated particles. Mica particles coated with surfactant adhesive protein without tyrosinase modification were washed out regardless of the amount of surfactant adhesive protein.

What is claimed is:

1. A surfactant adhesive protein comprising an amphiphilic peptide and an adhesive protein wherein the amphiphilic peptide is incorporated into the adhesive protein, wherein said adhesive protein is derived from mussel adhesive protein selected from the group consisting of FP-1 comprising at least one of the SEQ ID Nos: 1-3, FP-2 comprising SEQ ID No, 4, FP-3 comprising at least one of the SEQ ID NOs: 5-8, FP-4 comprising SEQ ID NO: 9, FP-5 comprising at least one of the SEQ ID NOs:10-13, FP-6 comprising SEQ ID NO: 14, FP-151 comprising at least one of the SEQ ID NOs; 15-17, FP-131 comprising SEQ ID NO:18 and FP-251 comprising SEQ ID NO:19, and wherein said amphiphilic peptide is selected from the group consisting of ARARADADARARADAD (SEQ ID NO: 20), EAEAKAKAEAEAKAKA (SEQ ID NO:21), QQRFQWQFEQQ (SEQ ID NO: 22), AEAEAKAK (SEQ ID NO:23), DPHHHWYHMHQH (SEQ ID NO: 24), HNWYHWWMPHNT (SEQ ID NO:25), HWKHPW-GAWDTL (SEQ ID NO: 26), HWSAWWIRSNQS (SEQ ID NO: 27), DDWSHWWRAWNG (SEQ ID NO: 28), YTSPWWLAWYDP (SEQ ID NO:29), AWWEAFIPNSIT (SEQ ID NO:30) and KLWKKWAKKWLKLWKA (SEQ ID NO:31); wherein optionally, if present, tyrosine residues among said adhesive protein are chemically modified to form DOPA (3,4-dibydroxphenylalanine) or DOPA-quinone.

2. The surfactant adhesive protein according to claim 1, wherein said amphiphilic peptide is incorporated into one or more sites selected from the group consisting of the C-terminus and N-terminus of said adhesive protein.

3. The surfactant adhesive protein according to claim 1, wherein said surfactant adhesive protein is fused with a biofunctional peptide.

4. The surfactant adhesive protein according to claim 3, wherein said biofunctional peptide is selected from the group consisting of an antimicrobial peptide, an antiviral peptide, an anticancer peptide, an anti-immune peptide, an anti-atopic peptide and an antithrombotic peptide.

5. The surfactant adhesive protein according to claim 4, wherein said anticancer peptide is composed of an amino acid sequence selected from the group consisting of SEQ ID NOs. 32-34.

6. The surfactant adhesive protein according to claim 4, wherein said antiviral peptide is composed of the amino acid sequence of SEQ ID NO. 35.

7. The surfactant adhesive protein of claim 1, wherein tyrosine residues among the amino acid residues of the adhesive protein are chemically modified to form DOPA (3,4-dihydroxyphenylalanine).

8. The surfactant adhesive protein of claim 7, wherein said DOPA is further chemically modified to convert to DOPA-quinone.

9. The surfactant adhesive protein of claim 7, wherein said chemical modification is conducted by tyrosinase.

10. A silicone oil comprising the surfactant adhesive protein according to claim 1 and mica particles, finely dispersed in a hydrophilic solvent.

11. The silicone oil according to claim 10, wherein said hydrophilic solvent is water or a water-containing solvent.

\* \* \* \* \*